United States Patent
Downing et al.

(10) Patent No.: US 9,533,146 B2
(45) Date of Patent: *Jan. 3, 2017

(54) SYSTEMS AND METHODS FOR FACILITATING APICAL ELECTRODE STIMULATION BY AN ELECTRO-ACOUSTIC STIMULATION SYSTEM

(71) Applicant: ADVANCED BIONICS AG, Staefa (CH)

(72) Inventors: Mark B. Downing, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/079,032

(22) Filed: Mar. 23, 2016

(65) Prior Publication Data

US 2016/0199647 A1    Jul. 14, 2016

Related U.S. Application Data (62) Division of application No. 14/375,123, filed as application No. PCT/US2012/023357 on Jan. 31, 2012, now Pat. No. 9,320,898.

(51) Int. Cl.
*A61N 1/36* (2006.01)
*H04R 25/00* (2006.01)
(Continued)

(52) U.S. Cl.
CPC ......... *A61N 1/36032* (2013.01); *A61N 1/0541* (2013.01); *A61N 1/37247* (2013.01);
(Continued)

(58) Field of Classification Search
CPC .................................................. A61N 1/36032
(Continued)

(56) References Cited

U.S. PATENT DOCUMENTS

| 5,776,179 A | 7/1998 | Ren et al. |
| 8,000,798 B2 | 8/2011 | Gantz et al. |

(Continued)

FOREIGN PATENT DOCUMENTS

| WO | WO-03/039660 | 5/2003 |
| WO | WO-2010/045358 | 4/2010 |

OTHER PUBLICATIONS

International Search Report and Written Opinion received in International Application No. PCT/US12/023357.
(Continued)

*Primary Examiner* — Allen Porter, Jr.
(74) *Attorney, Agent, or Firm* — ALG Intellectual Property, LLC (57) ABSTRACT

An exemplary system includes an electro-acoustic stimulation ("EAS") device, a cochlear implant, an electrode lead comprising a plurality of basal electrodes configured to be disposed within a basal region of a cochlea of a patient and a plurality of apical electrodes configured to be disposed within an apical region of the cochlea; and a loudspeaker communicatively coupled to the EAS device. The EAS device is configured to operate in an EAS mode by 1) disabling the apical electrodes for standard electrical stimulation, 2) detecting, while the apical electrodes are disabled for standard electrical stimulation, audio content presented to the patient and included in an acoustic stimulation frequency range, 3) directing the loudspeaker to apply acoustic stimulation representative of the audio content included in the acoustic stimulation frequency range to the patient, and 4) periodically directing the cochlear implant to apply
(Continued)

conditioning stimulation by way of the disabled apical electrodes.

20 Claims, 5 Drawing Sheets

(51) Int. Cl.
*A61N 1/05* (2006.01)
*A61N 1/372* (2006.01)
*H04R 25/02* (2006.01)

(52) U.S. Cl.
CPC ............ *H04R 25/02* (2013.01); *H04R 25/606* (2013.01); *H04R 2225/67* (2013.01)

(58) Field of Classification Search
USPC ........................................ 607/3, 56, 57, 137
See application file for complete search history.

(56) References Cited

U.S. PATENT DOCUMENTS

| | | |
|---|---|---|
| 2005/0033377 A1 | 2/2005 | Milojevic et al. |
| 2006/0287690 A1 | 12/2006 | Bouchataoui et al. |
| 2010/0094380 A1 | 4/2010 | Dadd |
| 2010/0280307 A1 | 11/2010 | Lineaweaver et al. |

OTHER PUBLICATIONS

Non-Final Office Action received in U.S. Appl. No. 14/375,123 dated Nov. 16, 2015.

Fig. 5

SYSTEMS AND METHODS FOR FACILITATING APICAL ELECTRODE STIMULATION BY AN ELECTRO-ACOUSTIC STIMULATION SYSTEM

RELATED APPLICATIONS

The present application is a divisional application of U.S. patent application Ser. No. 14/375,123, filed Jul. 28, 2014, which application is a U.S. National Stage Entry of PCT Application No. PCT/US2012/023357, filed Jan. 31, 2012. These applications are incorporated herein by reference in their respective entireties.

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

To facilitate electro-acoustic stimulation, a relatively short electrode lead is typically inserted into an EAS patient's cochlea such that electrodes disposed on the lead are located within the region of the cochlea that corresponds to the relatively high frequencies (i.e., the basal region). Unfortunately, however, the EAS patient may lose his or her residual hearing over time. As a result, it may be desirable for an EAS system to represent the low frequency audio content with electrical stimulation instead of with acoustic stimulation. To facilitate such electrical stimulation, the relatively short electrode lead must be replaced with a standard length electrode lead in order to place electrodes in the region of the cochlea that corresponds to the relatively low frequencies (i.e., the apical region).

To avoid the inconvenience, risks, and cost associated with replacing a relatively short electrode lead with a standard length electrode lead, an EAS patient could be fit originally with a standard length electrode lead, assuming the increased insertion depth does not cause damage to the cochlea structures. Electrodes located in the apical region are then disabled to facilitate electro-acoustic stimulation functionality of the EAS system. Unfortunately, biological buildup (e.g., protein buildup and/or buildup of other bodily matter) may accumulate on apical electrodes during extended periods of inactivity (e.g., while acoustic stimulation is still being employed by the EAS system). Such buildup may inhibit current flow through the apical electrodes and thereby render the apical electrodes useless for electrical stimulation when it becomes desirable for the EAS system to represent low frequency audio content with electrical stimulation instead of with acoustic stimulation. Moreover, extended periods of inactivity may result in diminished patency of the hearing nerve cells located in the vicinity of the apical electrodes.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for facilitating apical electrode stimulation by an electro-acoustic stimulation ("EAS") system are described herein. As will be described below, an exemplary EAS device may detect audio content presented to a patient and included in an acoustic stimulation frequency range, direct a loudspeaker to apply acoustic stimulation representative of the audio content included in the acoustic stimulation frequency range to the patient, and direct a cochlear implant implanted within the patient to apply sub-threshold electrical stimulation to the patient by way of one or more electrodes disposed within an apical region of a cochlea of the patient together with the application of the acoustic stimulation. Additionally or alternatively, the EAS device may periodically direct the cochlear implant to apply conditioning stimulation by way of the electrodes disposed within the apical region of the cochlea.

By applying sub-threshold electrical stimulation and/or conditioning stimulation to the one or more electrodes disposed within the apical region of the cochlea (i.e., to one or more "apical electrodes"), the systems and methods described herein may enhance the acoustic stimulation provided by an EAS system, maintain patency of the hearing nerve cells located in the vicinity of the apical electrodes (i.e., in the apical region of the cochlea), and prevent biological buildup from accumulating on the surfaces of the apical electrodes. Hence, effective electrical stimulation may be applied by the EAS system when it is deemed that the patient no longer benefits from acoustic stimulation.

Figure 1:
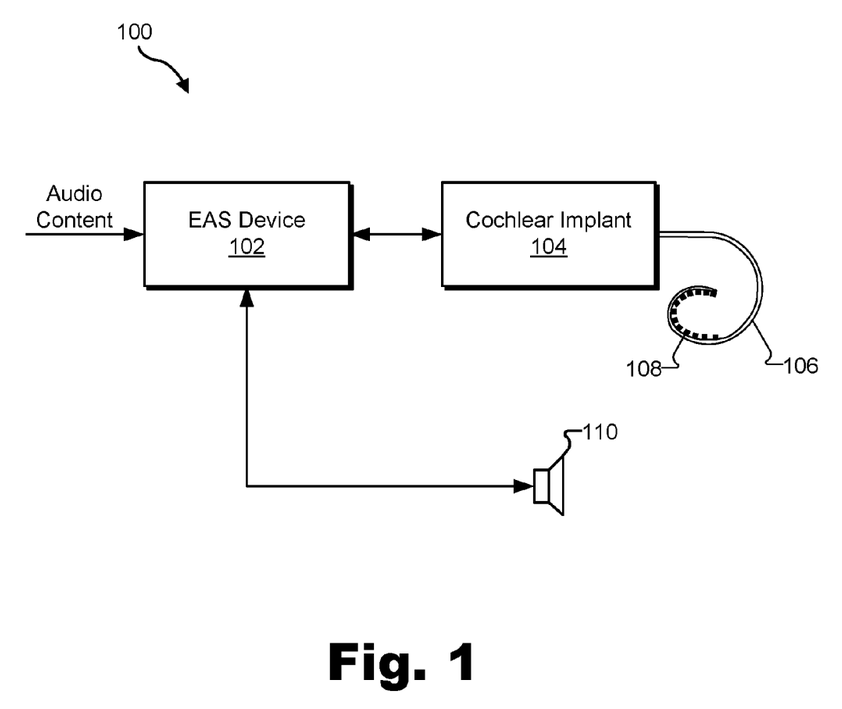
FIG. 1 illustrates an exemplary electro-acoustic stimulation system according to principles described herein.

FIG. 1 illustrates an exemplary EAS system 100. As shown, EAS system 100 may include an EAS device 102, a cochlear implant 104, an electrode lead 106 having a plurality of electrodes 108 disposed thereon, and a loudspeaker 110 (also referred to as a receiver).

EAS device 102 may include any suitable device configured to process audio content (e.g., one or more audio signals) presented to a patient and provide electrical and/or acoustic stimulation representative of the audio signals to the patient. In some examples, EAS device 102 may be implemented by an externally worn unit (e.g., a behind-the-ear device, a body worn device, etc.).

As mentioned, EAS device 102 may be used when the patient has some residual some hearing in the low frequencies (e.g., below 1000 Hz) and severe hearing loss in the high frequencies (e.g., above 1000 Hz). To this end, EAS device 102 may be configured to operate in an EAS mode by directing cochlear implant 104 to apply electrical stimulation representative of audio content included in a relatively high frequency band (e.g., above 1000 Hz) to one or more stimulation sites within the patient by way of one or more of electrodes 108 and directing loudspeaker 110 to apply acoustic stimulation representative of audio content included in a relatively low frequency band (e.g., below 1000 Hz) to the patient.

In some examples, EAS device 102 may be programmed to switch from operating in an EAS mode to operating in an electrical stimulation mode in which EAS device 102 directs cochlear implant 104 to apply electrical stimulation representative of audio content included in both the high and low frequency bands (to the exclusion of acoustic stimulation). For example, EAS device 102 may be programmed to switch from operating in an EAS mode to operating in an electrical stimulation mode when the patient loses his or her residual hearing.

Cochlear implant 104 may include any suitable auditory prosthesis configured to be at least partially implanted within a patient as may serve a particular implementation. For example, cochlear implant 104 may include an implantable cochlear stimulator, a brainstem implant and/or any other type of auditory prosthesis. EAS device 102 and cochlear implant 104 may communicate by way of any suitable wired or wireless communication channel.

Electrode lead 106 may be implanted within the patient such that electrodes 108 are in communication with stimulation sites within the cochlea. In this configuration, EAS device 102 may direct cochlear implant 104 to apply electrical stimulation representative of an audio signal to one or more stimulation sites within the patient by way of one or more of electrodes 108. As used herein, the term "in communication with" refers to electrodes 108 being adjacent to, in the general vicinity of, in close proximity to, directly next to, or directly on the one or more stimulation sites. Any number of electrodes 108 (e.g., sixteen) may be disposed on lead 106 as may serve a particular implementation.

Figure 2:
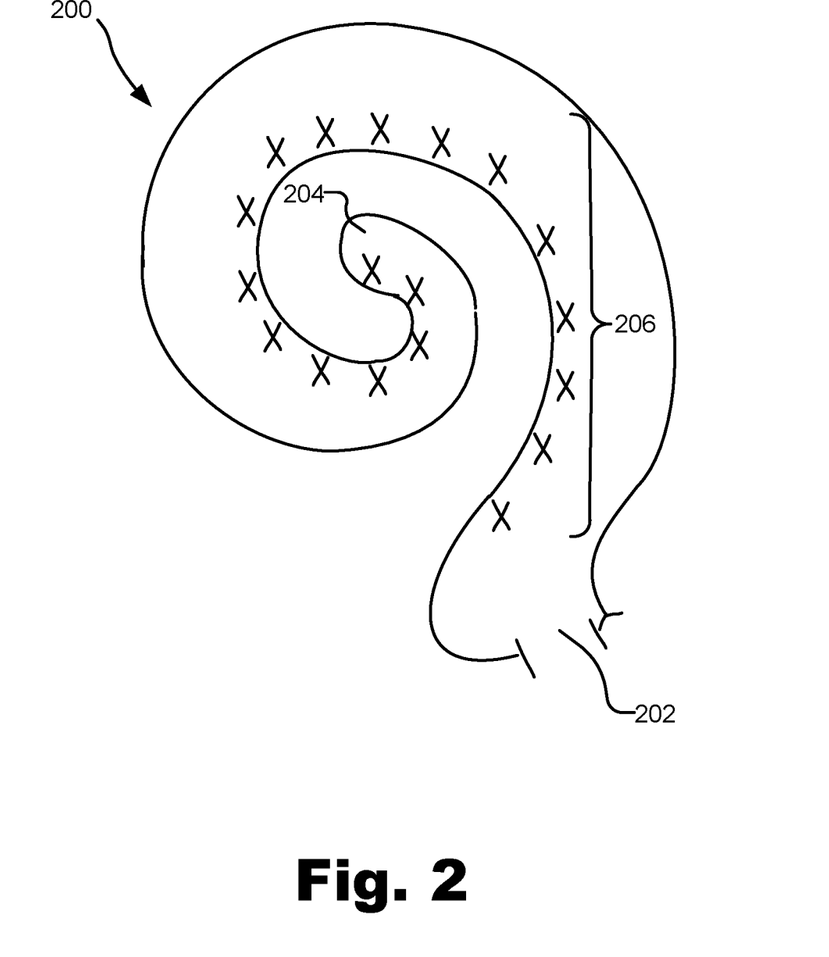
FIG. 2 illustrates a schematic structure of the human cochlea.

FIG. 2 illustrates a schematic structure of the human cochlea 200 into which lead 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Figure 3:
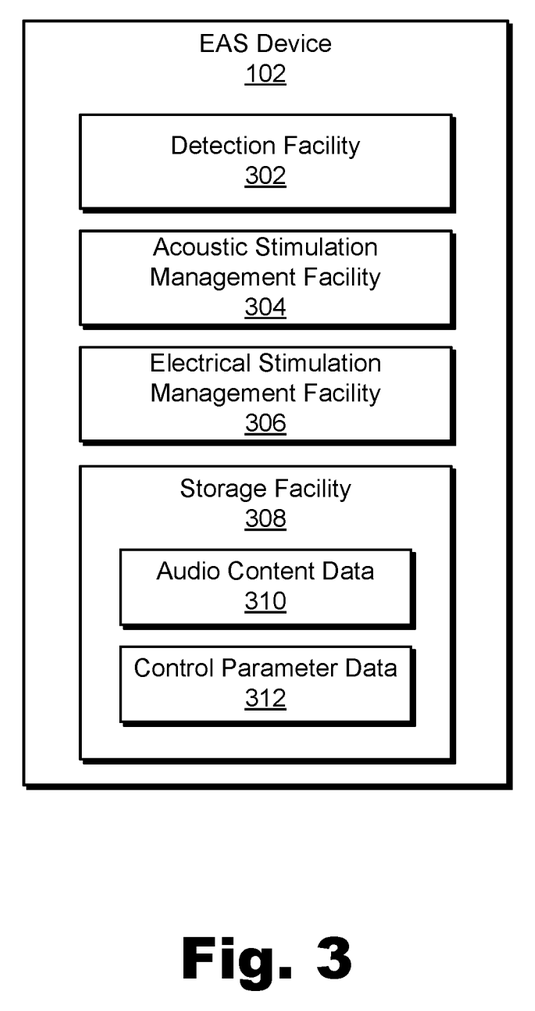
FIG. 3 illustrates exemplary components of an electro-acoustic stimulation device according to principles described herein.

FIG. 3 illustrates exemplary components of EAS device 102. As shown in FIG. 3, EAS device 102 may include a detection facility 302, an acoustic stimulation management facility 304, an electrical stimulation management facility 306, and a storage facility 308, which may be in communication with one another using any suitable communication technologies. One or more of facilities 302-308 may include one or more computing devices and/or processors configured to perform one or more of the functions described herein. Facilities 302-308 will now be described in more detail.

Detection facility 302 may be configured to detect audio content presented to a patient (e.g., one or more audio signals received by a microphone included within and/or communicatively coupled to EAS device 102) and one or more attributes associated with the audio content. For example, detection facility 302 may determine whether the detected audio content is included in an acoustic stimulation frequency range (i.e., a relatively low frequency range such as 100 Hz to 1 kHz) or an electrical stimulation frequency range (i.e., a relatively high frequency range such as 1 kHz to 8 kHz). If the detected audio content is included within the acoustic stimulation frequency range, the audio content may be represented to the patient in the form of acoustic stimulation. Alternatively, if the detected audio content is included within the electrical stimulation frequency range, the audio content may be represented to the patient in the form of electrical stimulation. As described above, the apical region of the cochlea is associated with the acoustic stimulation frequency range and the basal region of the cochlea is associated with the electrical stimulation frequency range.

Acoustic stimulation management facility 304 may be configured to perform one or more acoustic stimulation management operations. For example, acoustic stimulation management facility 304 may be configured to direct loudspeaker 110 to apply acoustic stimulation representative of audio content included in the acoustic stimulation frequency range to the patient. The directing may be performed in any suitable manner. For example, acoustic stimulation management facility 304 may direct loudspeaker 110 to apply the acoustic stimulation by transmitting one or more control signals to loudspeaker 110.

Electrical stimulation management facility 306 may be configured to perform one or more electrical stimulation management operations. For example, electrical stimulation management facility 306 may be configured to direct cochlear implant 104 to apply electrical stimulation representative of audio content included in the electrical stimulation frequency range to a patient. The directing may be performed in any suitable manner. For example, electrical stimulation management facility 306 may direct cochlear implant 104 to apply the electrical stimulation by transmitting one or more control signals to cochlear implant 104. Additional functions of electrical stimulation management facility 306 will be described below.

Storage facility 308 may be configured to maintain audio content data 310 representative of or otherwise associated with audio content detected by detection facility 302 and control parameter data 312 representative of one or more control parameters that may be transmitted to cochlear implant 104 and/or loudspeaker 110. Storage facility 308 may be configured to maintain additional or alternative data as may serve a particular implementation.

Various modes of operation of EAS device 102 will now be described. It will be recognized that the modes of operation described herein are merely illustrative of the many different modes in which EAS device 102 may operate in accordance with the systems and methods described herein.

In some examples, EAS device 102 may operate in accordance with an EAS mode. In this mode, the apical electrodes may be disabled for standard electrical stimulation (e.g., by EAS device 102, a fitting device, and/or in any other manner). With the apical electrodes disabled for standard electrical stimulation, EAS device 102 (i.e., electrical stimulation management facility 306) may abstain from directing cochlear implant 104 to apply electrical stimulation representative of audio content included in the frequency range associated with the apical electrodes (i.e., the acoustic stimulation frequency range) to the patient. Instead, EAS device 102 may direct loudspeaker 110 to apply acoustic stimulation representative of the audio content included in the frequency range associated with the apical electrodes to the patient.

While operating in the EAS mode, EAS device 102 may periodically direct cochlear implant 104 to apply conditioning stimulation by way of the disabled apical electrodes. As used herein, "conditioning stimulation" refers to any type of electrical stimulation configured to condition (i.e., maintain patency of or remove biological buildup from) the apical electrodes so that the apical electrodes may be available for future standard electrical stimulation (e.g., when EAS device 102 switches to operating in accordance with an electrical stimulation mode).

EAS device 102 may direct cochlear implant 104 to apply the conditioning stimulation in any suitable manner. For example, EAS device 102 may direct cochlear implant 104 to apply the conditioning stimulation in response to certain events (e.g., when EAS device 102 is powered on (e.g., when the patient puts EAS device 102 on in the morning after waking up), when EAS device 102 is coupled to a fitting device, when EAS device 102 switches to a different operating program, etc.). To this end, EAS device 102 (i.e., electrical stimulation management facility 306) may detect one of the events, temporarily enable the disabled apical electrodes in response to the detected event, direct cochlear implant 104 to apply conditioning stimulation by way of the temporarily enabled apical electrodes, and then disable the temporarily enabled apical electrodes upon completion of the application of the conditioning stimulation.

Additionally or alternatively, the conditioning stimulation may be applied by way of the apical electrodes while EAS device 102 is in operation (i.e., actively processing audio content and directing cochlear implant 104 and/or loudspeaker 110 to apply electrical and/or acoustic stimulation). For example, EAS device 102 may direct cochlear implant 104 to apply the conditioning stimulation at predetermined intervals (e.g., every few hours), even if EAS device 102 is in operation.

The conditioning stimulation applied by way of the apical electrodes may include any suitable type of electrical stimulation configured to condition the apical electrodes as may serve a particular implementation. For example, the conditioning stimulation may include bipolar stimulation (i.e., near-field current stimulation). Bipolar stimulation may be advantageous because relatively high amounts of current may be applied by way of the electrodes before the patient experiences a percept (i.e., before the patient perceives a sound or sensation associated with the application of the bipolar stimulation). Hence, the conditioning stimulation may be applied by way of the apical electrodes without the patient being aware of and/or affected by the conditioning stimulation. The conditioning stimulation may additionally or alternatively include monopolar stimulation, multipolar stimulation, and/or any other suitable type of stimulation as may serve a particular implementation.

Additionally or alternatively, EAS device 102 may direct cochlear implant 104 to apply sub-threshold electrical stimulation to the patient by way of one or more apical electrodes while EAS device 102 operates in accordance with the EAS mode. As used herein, "sub-threshold electrical stimulation" includes electrical stimulation that has a stimulation level that is less than a threshold level required for the patient to perceive the electrical stimulation.

For example, EAS device 102 (i.e., detection facility 302) may detect audio content presented to the patient and included in the acoustic stimulation frequency range. EAS device 102 (i.e., acoustic stimulation management facility 304) may then direct loudspeaker 110 to apply acoustic stimulation representative of the audio content included in the acoustic stimulation frequency range to the patient. EAS device 102 (i.e., electrical stimulation management facility 306) may also direct cochlear implant 104 to apply sub-threshold electrical stimulation to the patient by way of one or more apical electrodes together with (e.g., concurrently with) the application of the acoustic stimulation.

Application of sub-threshold electrical stimulation by way of one or more apical electrodes together with acoustic stimulation may provide various benefits to the patient. For example, the sub-threshold electrical stimulation may lower an acoustic detection threshold of the patient. As used herein, an "acoustic detection threshold" of a patient refers to a sound level of acoustic stimulation that is required for the patient to detect the acoustic stimulation. Application of sub-threshold electrical stimulation by way of one or more apical electrodes during application of acoustic stimulation may induce a stochastic response of the impaired cochlea, thereby resulting in a lowering of the patient's acoustic detection threshold.

Sub-threshold electrical stimulation may additionally or alternatively serve to maintain patency of hearing nerve cells located in the apical region of the cochlea of the patient. This is because the sub-threshold electrical stimulation may inhibit the neuropathy of such hearing nerve cells. Hence, when it comes time for EAS device 102 to switch to operating in an electrical stimulation mode, the hearing nerve cells located in the apical region may be more receptive of (i.e., respond more readily to) electrical stimulation representative of audio content included in the acoustic stimulation frequency range.

EAS device 102 may direct cochlear implant 104 to apply sub-threshold electrical stimulation to the patient by way of one or more apical electrodes together with the application of the acoustic stimulation in any suitable manner. For example, EAS device 102 may direct cochlear implant 104 to apply steady-state electrical stimulation by way of the one or more apical electrodes during the application of the acoustic stimulation. As another example, EAS device 102 may direct cochlear implant 104 to apply sporadic electrical stimulation by way of the one or more apical electrodes during the application of the acoustic stimulation. As another example, EAS device 102 may direct cochlear implant 104 to apply periodic electrical stimulation by way of the one or more apical electrodes during the application of the acoustic stimulation. Each type of sub-threshold electrical stimulation may include monopolar, bipolar, multipolar, and/or any other type of electrical stimulation as may serve a particular implementation.

In some examples, EAS device 102 may direct cochlear implant 104 to apply sub-threshold electrical stimulation to the patient by generating and transmitting one or more control parameters to cochlear implant 104. For example, EAS device 102 (i.e., electrical stimulation management facility 306) may generate one or more stimulation parameters configured to direct cochlear implant 104 to generate the sub-threshold electrical stimulation in a manner such that the sub-threshold electrical stimulation is configured to lower an acoustic detection threshold of the patient and/or maintain patency of hearing nerve cells located in the apical region of the cochlea of the patient. EAS device 102 may then transmit the one or more stimulation parameters to cochlear implant 104, which may use the one or more stimulation parameters to generate the sub-threshold electrical stimulation accordingly.

In some examples, EAS device 102 may direct cochlear implant 104 to generate and apply sub-threshold electrical stimulation that has a fixed stimulation level regardless of a sound level of the detected audio content. For example, the sub-threshold electrical stimulation may be configured to have a stimulation level that is a fixed proportion of the patient's acoustic detection threshold.

In some alternative examples, EAS device 102 may direct cochlear implant 104 to generate and apply sub-threshold electrical stimulation that has a variable stimulation level that depends on a sound level of the detected audio content. For example, the sub-threshold electrical stimulation may be configured to have a stimulation level that is based on a predetermined percentage of the sound level of the detected audio content.

As mentioned, EAS device 102 may be further configured to operate in accordance with an electrical stimulation mode in which EAS device 102 directs cochlear implant 104 to apply electrical stimulation representative of audio content included in both the high and low frequency bands (to the exclusion of acoustic stimulation). For example, EAS device 102 may switch from operating in an EAS mode to operating in an electrical stimulation mode when the patient loses his or her residual hearing when the patient no longer benefits from acoustic stimulation. The switch to the electrical stimulation mode may be performed in any suitable manner.

For example, EAS device 102 may switch to operating in accordance with an electrical stimulation mode by enabling the apical electrodes for electrical stimulation. EAS device 102 may then detect audio content included in the acoustic stimulation frequency range and direct cochlear implant 104 to apply electrical stimulation representative of the audio content to the patient by way of one or more of the apical electrodes.

Figure 4:
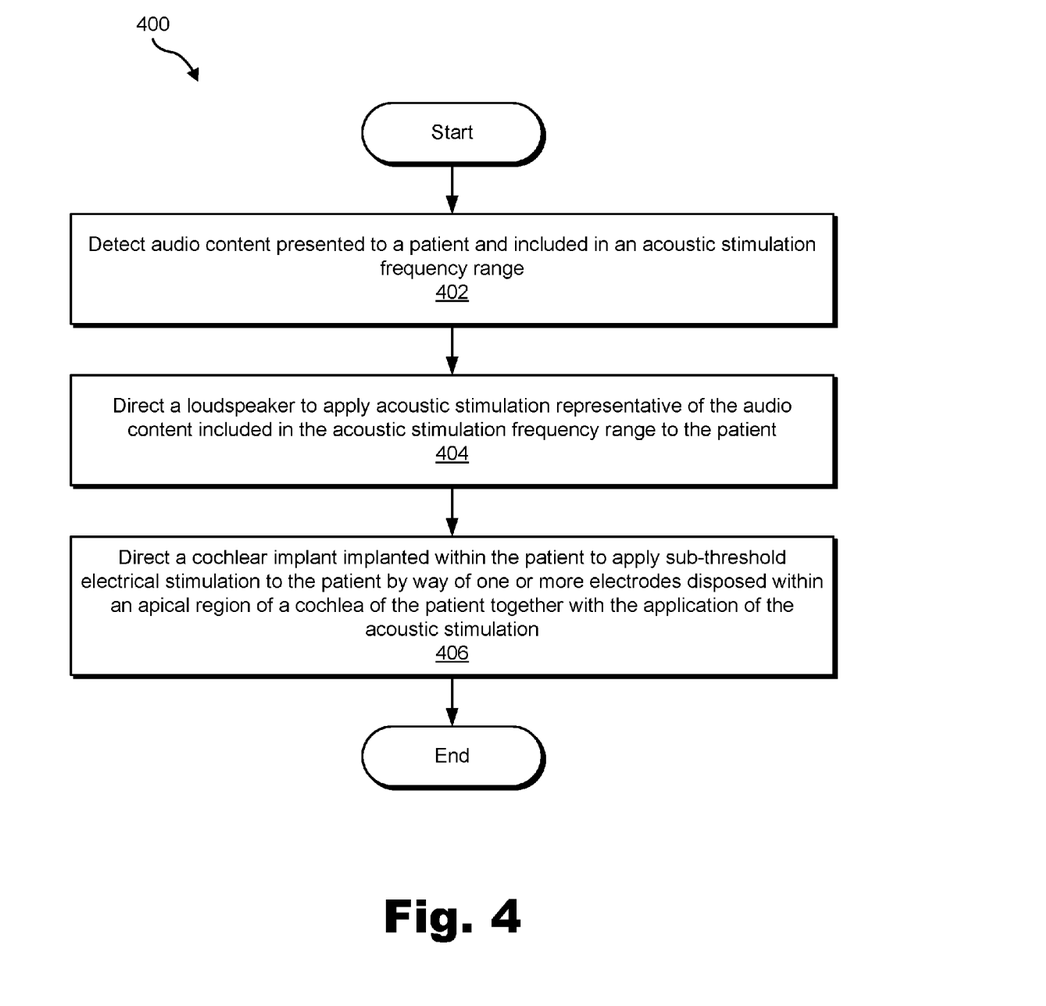
FIG. 4 illustrates an exemplary method of facilitating apical electrode stimulation by an electro-acoustic stimulation system according to principles described herein.

FIG. 4 illustrates an exemplary method 400 of facilitating apical electrode stimulation by an EAS system. While FIG. 4 illustrates exemplary steps according to one embodiment, other embodiments may omit, add to, reorder, and/or modify any of the steps shown in FIG. 4. One or more of the steps shown in FIG. 4 may be performed by an EAS device (e.g., EAS device 102).

In step 402, an EAS device detects audio content presented to a patient and included in an acoustic stimulation frequency range. Step 402 may be performed in any of the ways described herein.

In step 404, the EAS device directs a loudspeaker to apply acoustic stimulation representative of the audio content included in the acoustic stimulation frequency range to the patient. Step 404 may be performed in any of the ways described herein.

In step 406, the EAS device directs a cochlear implant implanted within the patient to apply sub-threshold electrical stimulation to the patient by way of one or more electrodes disposed within an apical region of a cochlea of the patient together with the application of the acoustic stimulation. Step 406 may be performed in any of the ways described herein.

Figure 5:
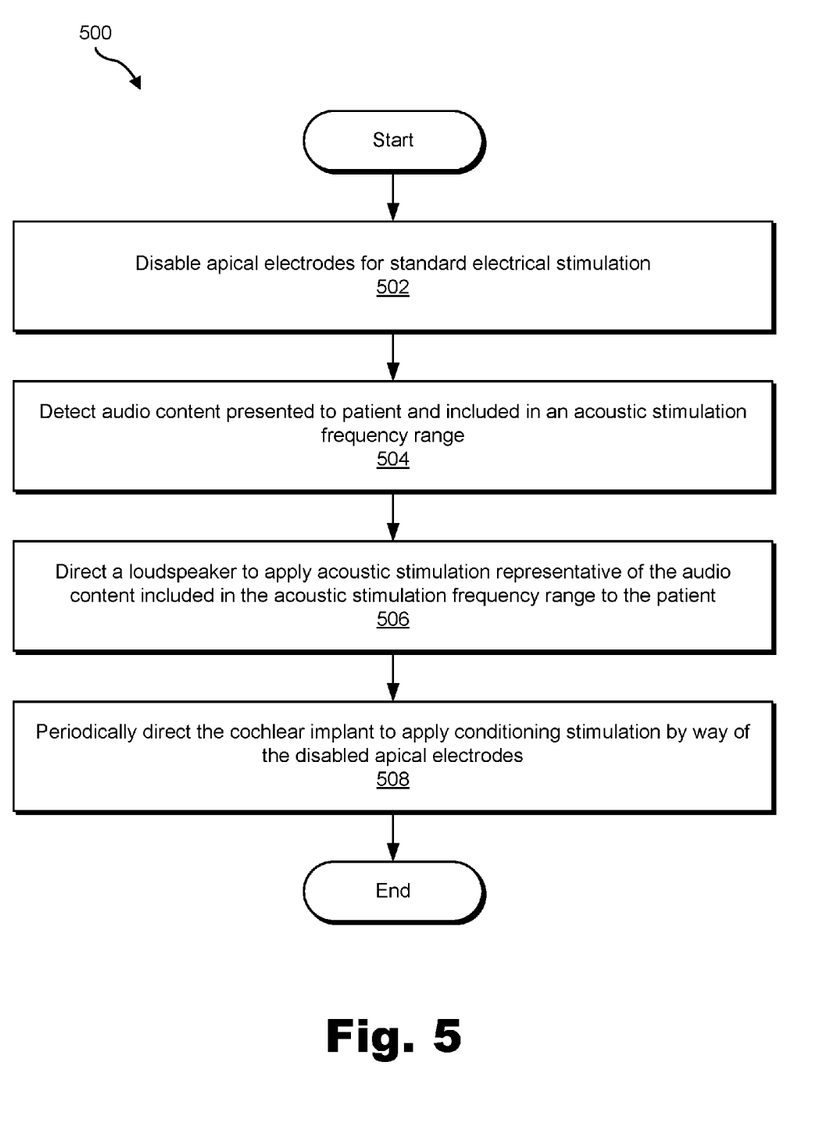
FIG. 5 illustrates another exemplary method of facilitating apical electrode stimulation by an electro-acoustic stimulation system according to principles described herein.

FIG. 5 illustrates another exemplary method 500 of facilitating apical electrode stimulation by an EAS system. While FIG. 5 illustrates exemplary steps according to one embodiment, other embodiments may omit, add to, reorder, and/or modify any of the steps shown in FIG. 5. One or more of the steps shown in FIG. 5 may be performed by an EAS device (e.g., EAS device 102).

In step 502, an EAS device disables apical electrodes for standard electrical stimulation. As described herein, the apical electrodes may be disposed on a lead that is inserted into the cochlea of a patient. Step 502 may be performed in any of the ways described herein.

In step 504, the EAS device detects audio content presented to the patient and included in an acoustic stimulation frequency range. Step 504 may be performed in any of the ways described herein.

In step 506, the EAS device directs a loudspeaker to apply acoustic stimulation representative of the audio content included in the acoustic stimulation frequency range to the patient. Step 506 may be performed in any of the ways described herein.

In step 508, the EAS device periodically directs the cochlear implant to apply conditioning stimulation by way of the disabled apical electrodes. Step 508 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   an electro-acoustic stimulation ("EAS") device;
   a cochlear implant communicatively coupled to the EAS device and configured to be implanted within a patient;
   an electrode lead communicatively coupled to the cochlear implant and comprising a plurality of basal electrodes configured to be disposed within a basal region of a cochlea of the patient and a plurality of apical electrodes configured to be disposed within an apical region of the cochlea; and
   a loudspeaker communicatively coupled to the EAS device;
   wherein the EAS device is configured to operate in an EAS mode by
      disabling the apical electrodes for standard electrical stimulation,
      detecting, while the apical electrodes are disabled for standard electrical stimulation, audio content presented to the patient and included in an acoustic stimulation frequency range,
      directing the loudspeaker to apply acoustic stimulation representative of the audio content included in the acoustic stimulation frequency range to the patient, and periodically directing the cochlear implant to apply conditioning stimulation by way of the apical electrodes that are disabled for standard electrical stimulation by
  detecting an event associated with the EAS device,
  temporarily enabling, in response to the detection of the event associated with the EAS device, the apical electrodes,
  directing the cochlear implant to apply the conditioning stimulation by way of the temporarily enabled apical electrodes, and
  disabling the temporarily enabled apical electrodes upon completion of the application of the conditioning stimulation.

2. The system of claim 1, wherein the EAS device is further configured to switch from operating in the EAS mode to operating in an electrical stimulation mode by
  enabling the apical electrodes for electrical stimulation;
  detecting additional audio content presented to the patient and included in the acoustic stimulation frequency range; and
  directing the cochlear implant to apply electrical stimulation representative of the additional audio content to the patient by way of one or more of the apical electrodes.

3. The system of claim 1, wherein the event associated with the EAS device comprises a powering on of the EAS device.

4. The system of claim 1, wherein the event associated with the EAS device comprises a switching of the EAS device to a different operating program.

5. The system of claim 1, wherein the event associated with the EAS device comprises a coupling of the EAS device to a fitting device.

6. The system of claim 1, wherein the EAS device is further configured to operate in the EAS mode by:
  detecting additional audio content presented to the patient and included in an electrical stimulation frequency range; and
  directing the cochlear implant to apply electrical stimulation representative of the additional audio content to the patient by way of one or more of the basal electrodes.

7. The system of claim 1, wherein the EAS device is further configured to direct the cochlear implant to apply, while the loudspeaker applies the acoustic stimulation to the patient and while the apical electrodes are disabled for standard electrical stimulation, sub-threshold electrical stimulation to the patient by way of one or more of the apical electrodes, the sub-threshold electrical stimulation comprising electrical stimulation not representative of the audio content and having a stimulation level that is less than a threshold level required for the patient to perceive the electrical stimulation.

8. A system comprising:
  an electro-acoustic stimulation ("EAS") device configured to operate in an EAS mode by
    disabling a plurality of apical electrodes for standard electrical stimulation, the apical electrodes included on an electrode lead that is communicatively coupled to a cochlear implant and configured to be disposed within an apical region of a cochlea of the patient, the electrode lead further comprising a plurality of basal electrodes configured to be disposed within a basal region of the cochlea of the patient,
    detecting, while the apical electrodes are disabled for standard electrical stimulation, audio content presented to the patient and included in an acoustic stimulation frequency range,
    directing a loudspeaker communicatively coupled to the EAS device to apply acoustic stimulation representative of the audio content included in the acoustic stimulation frequency range to the patient, and
    periodically directing the cochlear implant to apply conditioning stimulation by way of the apical electrodes that are disabled for standard electrical stimulation by
      detecting an event associated with the EAS device,
      temporarily enabling, in response to the detection of the event associated with the EAS device, the apical electrodes,
      directing the cochlear implant to apply the conditioning stimulation by way of the temporarily enabled apical electrodes, and
      disabling the temporarily enabled apical electrodes upon completion of the application of the conditioning stimulation.

9. The system of claim 8, wherein the EAS device is further configured to switch from operating in the EAS mode to operating in an electrical stimulation mode by
  enabling the apical electrodes for electrical stimulation;
  detecting additional audio content presented to the patient and included in the acoustic stimulation frequency range; and
  directing the cochlear implant to apply electrical stimulation representative of the additional audio content to the patient by way of one or more of the apical electrodes.

10. The system of claim 8, wherein the EAS device is further configured to direct the cochlear implant to apply, while the loudspeaker applies the acoustic stimulation to the patient and while the apical electrodes are disabled for standard electrical stimulation, sub-threshold electrical stimulation to the patient by way of one or more of the apical electrodes, the sub-threshold electrical stimulation comprising electrical stimulation not representative of the audio content and having a stimulation level that is less than a threshold level required for the patient to perceive the electrical stimulation.

11. The system of claim 8, wherein the event associated with the EAS device comprises a powering on of the EAS device.

12. The system of claim 8, wherein the event associated with the EAS device comprises a switching of the EAS device to a different operating program.

13. The system of claim 8, wherein the event associated with the EAS device comprises a coupling of the EAS device to a fitting device.

14. A method comprising:
  disabling, by an electro-acoustic stimulation ("EAS") device, a plurality of apical electrodes for standard electrical stimulation, the apical electrodes included on an electrode lead that is communicatively coupled to a cochlear implant and configured to be disposed within an apical region of a cochlea of the patient, the electrode lead further comprising a plurality of basal electrodes configured to be disposed within a basal region of the cochlea of the patient;
  detecting, by the EAS device while the apical electrodes are disabled for standard electrical stimulation, audio content presented to the patient and included in an acoustic stimulation frequency range;
  directing, by the EAS device, a loudspeaker communicatively coupled to the EAS device to apply acoustic stimulation representative of the audio content included in the acoustic stimulation frequency range to the patient, and periodically directing, by the EAS device, the cochlear implant to apply conditioning stimulation by way of the apical electrodes that are disabled for standard electrical stimulation by
- detecting an event associated with the EAS device,
- temporarily enabling, in response to the detection of the event associated with the EAS device, the apical electrodes,
- directing the cochlear implant to apply the conditioning stimulation by way of the temporarily enabled apical electrodes, and
- disabling the temporarily enabled apical electrodes upon completion of the application of the conditioning stimulation.

15. The method of claim 14, further comprising switching, by the EAS device, to operating in an electrical stimulation mode by:
- enabling the apical electrodes for electrical stimulation;
- detecting additional audio content presented to the patient and included in the acoustic stimulation frequency range; and
- directing the cochlear implant to apply electrical stimulation representative of the additional audio content to the patient by way of one or more of the apical electrodes.

16. The method of claim 14, wherein the event associated with the EAS device comprises a powering on of the EAS device.

17. The method of claim 14, wherein the event associated with the EAS device comprises a switching of the EAS device to a different operating program.

18. The method of claim 14, wherein the event associated with the EAS device comprises a coupling of the EAS device to a fitting device.

19. The method of claim 14, further comprising:
- detecting, by the EAS device, additional audio content presented to the patient and included in an electrical stimulation frequency range; and
- directing, by the EAS device, the cochlear implant to apply electrical stimulation representative of the additional audio content to the patient by way of one or more of the basal electrodes.

20. The method of claim 14, further comprising directing, by the EAS device, the cochlear implant to apply, while the loudspeaker applies the acoustic stimulation to the patient and while the apical electrodes are disabled for standard electrical stimulation, sub-threshold electrical stimulation to the patient by way of one or more of the apical electrodes, the sub-threshold electrical stimulation comprising electrical stimulation not representative of the audio content and having a stimulation level that is less than a threshold level required for the patient to perceive the electrical stimulation.

* * * * *